United States Patent [19]

Keyes

[11] 4,194,067

[45] Mar. 18, 1980

[54] PROCESS FOR THE PURIFICATION OF CARBOHYDRATE CONTAINING ENZYMES

[75] Inventor: Melvin H. Keyes, Sylvania, Ohio

[73] Assignee: Technicon Instruments Corp., Tarrytown, N.Y.

[21] Appl. No.: 929,477

[22] Filed: Jul. 31, 1978

[51] Int. Cl.$^2$ ............................................. C07G 7/00

[52] U.S. Cl. ................................... 435/190; 435/192; 435/189; 435/262; 435/814

[58] Field of Search .................................. 195/66 R, 4

[56] References Cited

PUBLICATIONS

Nakamura et al., in FEBS Letters, vol. 41, No. 2, pp. 327–330, May 1974.

*Primary Examiner*—Lionel M. Shapiro
*Attorney, Agent, or Firm*—S. P. Tedesco

[57] ABSTRACT

This invention relates to a method for purifying a carbohydrate containing enzyme which is a desired enzyme preferred to be separated from a mixture. The method comprises the steps of mixing a solution containing the carbohydrate containing enzyme with a carbohydrate modifying reagent. The carbohydrate modifying reagent reacts with the carbohydrate attached to the enzyme, thereby modifying its chemical structure. The modified enzyme is then separated from the other undesirable enzymes or proteins in the mixture by a suitable chemical separation method, for example, gel filtration chromatography. The method was used in the separation of glucose oxidase from catalase, a separation which by previous methods was very inefficient.

17 Claims, No Drawings

PROCESS FOR THE PURIFICATION OF CARBOHYDRATE CONTAINING ENZYMES

BACKGROUND OF THE INVENTION

1. Field Of The Invention.

This invention relates to a method for the chemical purification of enzymatic proteins. Known chemical separation methods for enzymatic proteins are usually based upon differential precipitation of the preferred enzyme from other undesirable enzymes and impurities which contaminate the mixture. Where an enzyme is not separable from other impurities found in the enzyme mixture, in many cases this renders it useless in particular applications. For example, the enzyme, glucose oxidase, is usually found in the presence of the enzyme catalase. Glucose oxidase contains a carbohydrate moiety and is thus a carbohydrate containing enzyme. Glucose oxidase catalyzes the reaction of glucose to form gluconic acid and hydrogen peroxide. Catalase catalyzes the degradation of hydrogen peroxide. In many applications glucose oxidase is used to generate hydrogen peroxide to quantify the glucose substrate. When catalase is present the hydrogen peroxide generated by the glucose oxidase is partially destroyed. The method is thus less accurate and in many cases totally ineffective. Other examples are known where one enzyme is extremely difficult to separate from another and this inability to separate the enzymes limits the utility of the preferred enzyme.

Additionally, presently known methods of separating enzymes are time consuming, possibly on the order of hours, usually require a number of different reagents to complete the separations process, and result in a low yield of the separated preferred enzyme. These drawbacks in the cases where separation is possible as well as the circumstance where separation is not completely possible, or possible only with very undesirable levels of contaminants, are overcome by the present invention.

2. Description Of The Prior Art.

Most of the known prior art relating to the chemical separation of enzymes from other enzymes or other chemical impurities in a mixture are concerned primarily with three methods of separation. The first method is differential precipitation, using water-miscible solvents. U.S. Pat. No. 3,616,232 discloses the use of water-miscible alkanols, alkylketones, and cyclic ethers as precipitating agents to separate proteins. The solution containing the proteins is mixed with the water-miscible solvents, in which the enzymes themselves are not soluble, in a particular volume to volume fraction. After the solvents are added, the mixture is shaken, and at particular volume to volume fractions different proteins fractionate from the mixture. Similarly, U.S. Pat. Nos. 3,645,851 and 2,926,122 disclose the use of low molecular weight alcohols to differentially precipitate proteins from an aqueous solution, and then collect the precipitated proteins. Most of these differential solvent precipitation methods require precise balancing of solvent volumes, solution temperatures, and the time the solutions are allowed to stand. These methods always involve the inherent risk of solvent denaturation of the enzyme or protein which is preferred and is being recovered. Additionally, these methods usually take long periods of time and in many cases have low yields of the preferred enzyme.

The second commonly used separation method of enzyme or protein purifcation involves differential precipitation without the use of solvents. In these methods, generally speaking, an inorganic salt or organic base is added to a solution of the preferred enzyme. The preferred enzyme or the contaminating enzymes are differentially precipitated from the solution. The precipitate or the supernatant liquid, whichever contains the preferred enzyme, is then processed by known chemical methods, for example, gel filtration. These methods also usually require long periods of time, the separation and handling of precipitates, and generally use a number of reagents. For example, U.S. Pat. No. 3,930,953 discloses the precipitation of glucose oxidase from an aqueous solution by mixing the glucose oxidase solution with diaminoethoxyacridine lactate. The lactate forms a precipitate with the glucose oxidase. The solution is allowed to stand for as long as twenty-four hours at low temperatures, whereupon the lactate-protein complex precipitates out of solution. The complex is then recovered and destroyed by the addition of large quantities of chloride salts and the resultant free glucose oxidase is separated by conventional chemical methods. Similarly with U.S. Pat. Nos. 3,265,587 and 3,269,918 the desired protein is precipitated or the impurities are precipitated and the fraction containing the desired protein is further processed by conventional chemical methods. Typical precipitating reagents are calcium, barium, and ammonium sulfates.

The third type of known separation method comprises contacting the enzyme mixture with a solution containing an insolublized coenzyme, which is reacted with respect to one or more of the enzymes in the mixture. The enzyme in the mixture becomes attached to the insolubilization support through the coenzyme. The support is removed from the mixture with the enzyme attached thereto, and the enzyme is eluted from the support for further processing.

None of the prior art discussed above discloses a method for the separation of carbohydrate containing proteins wherein the carbohydrate portion of the carbohydrate containing preferred enzyme is modified. The process, according to the present invention, is very rapid compared to methods known in the art. Also, the method is relatively inexpensive and has a very high yield of the preferred enzyme. In many cases, substantially all of the preferred enzyme is isolated from impurities, with yields of the preferred enzyme on the order of 90% recovery and above.

Additional references to precipitation methods of purification of proteins of enzymatic types are: "The Oxidation of Glucose and Related Compounds by Glucose Oxidase from *Aspergillus niger*". John H. Pazur and Kjell Kleppe, Biochemistry, Vol. 3, pp. 578-83 (1964); "Purification and Properties of the Glucose Oxidase from *Aspergillus niger*" Bennett E. P. Swoboda and Vincent Massey, Journal of Biological Chemistry, Vol. 240, pp. 2209-15 (1965); "Comparative Studies on the Glucose Oxidase of *Aspergillus niger* and *Penicelium amagasakiense*" Satoshi Nakamura and Smiko Fujiki, Journal of Biochemistry, Vol. 63, pp. 51-8 (1968); and "The Glucose Oxidase Mechanism, Interpretation of the pH Dependence", Michael K. Weibel and Harold J. Bright, Journal of Biological Chemistry, Vol. 246, pp. 2734–44 (1971).

It has been recognized that carbohydrate moieties on carbohydrate containing enzymes can be treated with oxidizing agents preparatory to immobilization by covalent bonding to supports. See, "The Immobilization of Glucose Oxidase. Activation of its Carbohydrate Residues", O. R. Zaborsky and J. Ogletree, Biochem. Biophys. Res. Commun., Vol. 61, pp. 210-16 (1974).

Also, the oxidation of carbohydrate moities on proteins has been accomplished in order to determine kinetic and structural properties of proteins in solution. For examples of such determinations see, "A Role of the Carbohydrate Moiety of Glucose Oxidase: Kinetic Evidence for Protection of the Enzyme from Thermal Inactivation in the Presence of Sodium Dodecyl Sulfate", S. Kakamura and S. Hayashi, FEBS Letters, Vol. 41, pp. 327-9 (1974), and "The Composition and Structure of Carbohydrate Moiety of Stem Bromelain", Y. Yasuda, N. Takahashi, and T. Murachi, Biochemistry, Vol. 9, pp. 25-32 (1970).

Based on the above discussed art, no method is believed known for the separation of a carbohydrate containing enzymatically active protein from a contaminating protein or enzyme by the modification of the carbohydrate moiety according to the method of the present invention.

SUMMARY OF THE INVENTION

It is an object of this invention to provide a method to separate carbohydrates containing enzymes from contaminating enzymes and in particular, the enzyme catalase.

Another object of this invention is to provide an enzyme separation method whereby carbohydrate containing enzymes may be rapidly separated from contaminating enzymes.

A further object of this invention is to provide a method for separating carbohydrate containing enzymes from contaminating enzymes using a minimum of externally supplied reagents.

An additional object of this invention is to provide the rapid low cost method described above which is capable of producing high yields of the carbohydrate containing enzyme with high activities in the final isolated enzymes.

These and other objects are accomplished by a method for separating a carbohydrate containing enzyme from a contaminating enzyme, particularly catalase, comprising the steps of, mixing the solution containing the carbohydrate containing enzyme with a carbohydrate modifying reagent. The solution is allowed to react for a period of time sufficient to allow the modifying reagent to modify the carbohydrate attached to the enzyme. The modified carbohydrate containing enzyme and contaminating enzyme are then subjected to conventional method of chemical separation. Particularly preferred is gel filtration chromatography, which has been demonstrated to give very high yields of the preferred protein at high activity levels.

Note that a feature of this invention is that certain carbohydrate containing enzymes (or proteins which are nonenzymatic), for example, glucose oxidase, have been discovered by this method to be more readily separable from contaminating enzymes such as catalase when the carbohydrate moiety is modified.

The method according to the present invention shows excellent reproducibility over wide ranges of catalase and glucose oxidase concentrations, and can be used with relatively inexpensive, readily available laboratory reagents.

DETAILED DESCRIPTION OF THE INVENTION

The present method is particularly useful and successful in the separation of glucose oxidase, a carbohydrate containing enzyme, in impure form from contaminating catalase. The discussion will be directed particularly toward experimental results and information concerning the proteins glucose oxidase and catalase, but it is to be understood that the method of the present invention is equally applicable to any carbohydrate containing enzymatic protein or nonenzymatic protein which can be treated in accordance with the method of the invention.

Glucose oxidase has a carbohydrate moiety which is approximately 16% by weight of the glucose oxidase molecule in its native state.

It has been discovered in the present invention that there seems to be some form of molecular interaction between the glucose oxidase/carbohydrate molecule and the enzyme catalase. It is believed that this interaction causes much of the difficulty which is traditionally encountered when attempting to purify glucose oxidase from catalase. While not being bound by any theory, it is clear from the experimental evidence presented hereinafter that glucose oxidase when treated according to the method of the present invention is more effectively separable from catalase than by previous methods. The method of the present invention works equally well with members of the enzyme class known as dehydrogenases.

In a preferred embodiment of the invention a solution of the glucose oxidase is treated with a hydrolytic enzyme which is capable of at least partially hydrolyzing the carbohydrate moiety attached to the main body of the glucose oxidase molecule. In any case, the hydrolytic enzyme reacts with the carbohydrate moiety for a controlled period of time. If the reaction time is extended long enough the entire carbohydrate moiety can be removed from the carbohydrate containing enzyme. However, in other instances, the time may be shortened to a time that allows only sufficient enzymatic modification of the carbohydrate moiety to achieve the results of facilitating separation of the glucose oxidase from the catalase. Enzymes which have shown good results, as hydrolytic enzymes to hydrolyze the carbohydrate moiety are dextranase, amylase, glucoamylase and cellulase. Dextranase has been shown particularly useful in the preferred embodiment and will be exemplified hereinafter.

To employ the method, a solution of the glucose oxidase is incubated with a solution containing dextranase or one of the other enzymes capable of at least partially hydrolyzing the carbohydrate moiety of the glucose oxidase, for example, an amylase, cellulase or glucoamylase. The incubation solution is typically at about pH 3.8 and between 35° and 40° C. After the reaction is started the mixture may be allowed to stand overnight unattended and processed the next day. After the incubation is completed the solution containing the glucose oxidase, now having a modified carbohydrate moiety, is applied to a gel filtration chromatography column and fractions eluted from the column are analyzed at 254 nm to detect the glucose oxidase fraction. It has been demonstrated that glucose oxidase on the order of 95% purity may be obtained using conventionally available Sephadex or Sepharose columns. Sephadex and Sepharose gels are cross-linked highly hydrated polymeric dextran gels.

In an alternative embodiment of the present invention, the carbohydrate moiety on the glucose oxidase is treated with sodium periodate. The sodium periodate is believed to partially oxidize the carbohydrate moiety, thereby, it is assumed, reducing its role in causing the catalase to interact with the glucose oxidase.

In the alternative embodiment a solution of the glucose oxidase with the carbohydrate moiety attached is mixed with sodium periodate until the periodate concentration is approximately 1/10th molar. The solution is stirred for about two hours at approximately 0° C. The reaction is quenched by the addition of 15 ml of ethylene glycol. The reaction may be quenched in any acceptable fashion. The resultant solution is believed to contain glucose oxidase with its carbohydrate moiety partially oxidized. This mixture is eluted from a Sephadex or Sepharose column as is the material from the enzymatic hydrolysis embodiment. The material thus eluted was found to be on the order of 90% pure with respect to glucose oxidase.

To demonstrate the effectiveness of the present method in separating a carbohydrate containing protein, such as glucose oxidase from catalase, reference is made to Tables I, II and III. The Tables each show the number of fractions collected upon elution of the material from the designated procedures from a gel filtration chromatography column. The first column of each Table indicates the fraction number which is received from the column. The second column indicates the absolute absorbance value for each fraction, the third column indicates the activity level of the glucose oxidase for each fraction, and the fourth column indicates the catalase activity for each fraction.

The materials used in Table I were a column packed with Sepharose 4 B gel onto which was applied approximately 5 ml of glucose oxidase solution (Miles-Servac, *Aspergillus niger*). The enzyme was eluted using $5 \times 10^{-3}$ molar succinic acid buffer and $5 \times 10^{-3}$ molar EDTA, at about pH 5. The fractions are collected by allowing the fluids placed on the column to elute and collect separate fractions in separate analysis tubes.

Table I shows the results of the chromatography of glucose oxidase which is contaminated with catalase when the solution has not been treated according to either embodiment of the present invention. The data shows that there is a very inefficient separation of the glucose oxidase from the catalase using conventional gel chromatography alone. Each fraction of Table I represents 10 ml of eluent from the column. As indicated by Table I, 3 fractions are found to contain substantial amounts of glucose oxidase. Each of these fractions also has substantial amounts of contaminating catalase. Fraction 3, the fraction lowest in catalase activity, shows approximately 20% of the total enzymatic activity as being due to catalase. This high catalase contamination value is typical of the level of catalase contamination when normal gel chromatography methods are used. This Table serves to show that glucose oxidase purified using gel chromatography is not effectively purified, and not suitable for many uses.

TABLE I

| | GEL FILTRATION WITHOUT MODIFICATION | | |
|---|---|---|---|
| Fraction | Absorbance at 254 nm | Glucose Oxidase U/mg Protein | Catalase U/mg Protein |
| 1 | 0.010 | 47 | 14 |

TABLE I-continued

| | GEL FILTRATION WITHOUT MODIFICATION | | |
|---|---|---|---|
| Fraction | Absorbance at 254 nm | Glucose Oxidase U/mg Protein | Catalase U/mg Protein |
| 2 | 0.030 | 18 | 14 |
| 3 | 2.0 | 19 | 5 |

The materials and methods used to generate Table II include the use of 10 ml fractions of glucose oxidase (Miles-Servac, *Aspergillus niger*) which are added to 3 to 5 ml of dextranase solution (5 mg per ml, Dextranase Products, Ltd.). The pH of the solution was adjusted to about 3.8 and was allowed to incubate overnight at a temperature of between 35° and 40° C. The reaction was monitored by an oxygen monitoring electrode. As the carbohydrate is hydrolyzed by the dextranase free glucose is liberated. The glucose oxidase then degrades the glucose to form gluconic acid and hydrogen peroxide, using molecular oxygen found in the solution. As the oxygen concentration decreases this indicates hydrolysis of the carbohydrate and indicates approximately when the reaction has gone to completion. Approximately 5 ml of the glucose oxidase solution was applied to a column containing Sepharose 4 B material. As indicated by the results the improved separation of glucose oxidase is substantial.

Table II shows the effect on gel filtration purification of the modification of the carbohydrate containing enzyme which has been incubated with a dextranase enzyme to at least partially hydrolyze the carbohydrate moiety on the glucose oxidase. The fractions in Table II are again 10 ml fractions, with the same column headings as Table I. The difference between the experiments represented by Tables I and II is that the dextranase treatment sample shows very much better separation of the glucose oxidase from the catalase. Notice that fractions 2, 3 and 4 are extremely high in glucose oxidase activity while being extremely low in catalase activity. Based on activity measurements, the fraction collected in tubes 2 and 4 are about 95% pure in glucose oxidase, while the fraction collected in tube 3 is about 94% pure in glucose oxidase. This indicates that the dextranase treatment according to the present invention does in fact substantially increase not only the yield of glucose oxidase, which may be gained from purification process, but also substantially increases the relative purity of the glucose oxidase isolated. Notice that the improvement over the results of Table I is approximately 15%, representing a substantial advantage over the known methods.

TABLE II

| | GEL FILTRATION WITH DEXTRANASE MODIFICATION (CARBOHYDRATE HYDROLYSIS) | | |
|---|---|---|---|
| Fraction | Absorbance At 254 nm | Glucose Oxidase U/mg Protein | Catalase U/mg Protein |
| 1 | .003 | 74 | 55 |
| 2 | .021 | 38 | 1.8 |
| 3 | .019 | 48 | 3 |
| 4 | .009 | 99 | 4.9 |
| 5 | .008 | 63 | 51 |

The materials and methods used to generate Table III include the use of about 30 ml of glucose oxidase solution, to which is added enough sodium periodate to bring the solution to 0.1 M in periodate. The solution is allowed to react for about two hours at about 0° C. and then applied to the column.

Table III represents the alternative embodiment of the present invention, using an inorganic oxidizing agent as the chemical oxidant, in this case sodium periodate. The headings of each column are the same as Tables I and II with the exception that the adsorbance is measured at 280 nm and the fraction size is 13 ml. As indicated by fractions 4, 5 and 6, glucose oxidase may be obtained which is approximately 91%, 89%, 86% pure as compared to the maximum results of approximately 80% using standard gel filtration techniques. This indicates again the substantial increase in the purity of glucose oxidase when processed according to the methods of the present invention.

TABLE III
GEL FILTRATION WITH SODIUM PERIODATE MODIFICATION (PARTIAL OXIDATION)

| Fraction | Absorbance at 280 nm | Glucose Oxidase U/mg Protein | Catalase U/mg Protein |
|---|---|---|---|
| 1 | 0.165 | 18 | 50 |
| 2 | 0.360 | 21 | 29 |
| 3 | 0.340 | 31 | 18 |
| 4 | 0.300 | 77 | 8 |
| 5 | 0.250 | 46 | 6 |
| 6 | 0.190 | 60 | 10 |
| 7 | 0.200 | 39 | 10 |
| 8 | 0.260 | 30 | 8 |
| 9 | 0.130 | 56 | 19 |
| 10 | 0.10 | 59 | 22 |

The following Examples illustrate the procedures used to produce the purified glucose oxidase according to the methods of the present invention.

EXAMPLE I

Ten ml of glucose oxidase (Miles-Servac, *Aspergillus niger*) solution was added to 3 to 5 ml of dextranase solution (5 mg per ml, Dextran Products, Ltd.). The pH of the solution is adjusted to approximately 3.8 and the temperature adjusted to between 35° and 40° C. The oxygen concentration of the reaction mixture is monitored overnight and when the oxygen concentration has decreased to a significant level, 5 ml of the glucose oxidase solution is applied to a Sepharose 4 B column. The column is eluted with $5 \times 10^{-3}$ molar succinic acid buffer and $5 \times 10^{-3}$ molar EDTA, at about pH 5. The material effluent from the column is represented in Table II. The identical procedure may be performed with glucoamylase, amylase, or cellulase, with substantially identical results being produced.

EXAMPLE 2

Thirty ml of a solution of glucose oxidase (Miles-Servac, *Aspergillus niger*) is placed in a clean dry beaker. Enough solid sodium periodate (reagent grade) is added to the 30 ml of glucose oxidase solution to bring the concentration of the periodate to 0.1 molar. The solution is stirred for approximately 2 hours at about 0° C. The reaction is quenched with the addition of 15 ml of ethylene glycol, and 5 ml of the solution is applied to a Sepharose 4B column. The column is eluted with $5 \times 10^{-3}$ molar succinic acid buffer and $5 \times 10^{-3}$ molar EDTA, at about pH 5. The material eluted from the column produced the results shown in Table III.

In accordance with the provisions of the patent statutes the principles and mode of operation of the invention has been illustrated and described in what is considered to be its best embodiments. It is understood that, within the scope of the appended claims, the invention may be practiced otherwise than specifically illustrated, and described in the typical embodiments and accompanying alternatives herein.

What is claimed is:

1. A method for separating a carbohydrate containing enzyme from the enzyme catalase, comprising:
   a. mixing a solution containing said carbohydrate containing enzyme with a carbohydrate modifying reagent,
   b. allowing said carbohydrate containing enzyme and said modifying reagent to react to modify said carbohydrate,
   c. and separating said enzyme from said catalase enzyme.

2. The method of claim 1 wherein said modifying agent oxidizes said carbohydrates on said carbohydrate containing enzyme.

3. The method of claim 2 wherein said modifying reagent is an inorganic oxidizing agent.

4. The method of claim 3 wherein said oxidizing agent is sodium periodate.

5. The method of claim 1 wherein said modifying reagent is an enzyme.

6. The method of claim 5 wherein said enzyme is a dextranase.

7. The method of claim 5 wherein said enzyme is an amylase.

8. The method of claim 5 wherein said enzyme is a cellulase.

9. The method of claim 5 wherein said enzyme is a glucoamylase.

10. The method of claim 1 wherein said carbohydrate containing enzyme is an oxidase.

11. The method of claim 10 wherein said oxidase is glucose oxidase.

12. The method of claim 1 wherein said carbohydrate containing enzyme is a dehydrogenase.

13. The method of claim 1 wherein said separation of said enzyme from said catalase enzyme is conducted by gel filtration chromatography procedures.

14. A method for separating glucose oxidase contained in an enzyme mixture with catalase comprising:
   a. adding to said mixture an aqueous solution of dextranase,
   b. allowing said mixture and dextranase to react thereby removing the carbohydrate from the glucose oxidase, and
   c. separating said carbohydrate-free glucose oxidase from said reacted mixture.

15. The method of claim 14 wherein said dextranase is immobilized on a solid support in said aqueous solution.

16. The method of claim 15 wherein said dextranase is separated from said reacted mixture by filtration, and said carbohydrate-free glucose oxidase and catalase are separated by gel filtration chromatography procedures.

17. A method for separating glucose oxidase contained in an enzyme mixture with catalase comprising adding to said mixture an aqueous solution of sodium periodate in an amount sufficient to react and partially oxidize the carbohydrate of said glucose oxidase, and separating said oxidized carbohydrate-containing glucose oxidase from said reacted mixture by gel filtration chromatography.

* * * * *